United States Patent [19]
Press et al.

[11] Patent Number: 5,398,676
[45] Date of Patent: * Mar. 21, 1995

[54] PORTABLE EMERGENCY RESPIRATOR

[76] Inventors: Roman J. Press, 20 Sutton Pl., Rochester, N.Y. 14620; Jeffrey S. Gutterman, 100 Hogan Point Rd., Hilton, N.Y. 14468

[*] Notice: The portion of the term of this patent subsequent to May 18, 2010 has been disclaimed.

[21] Appl. No.: 130,107

[22] Filed: Sep. 30, 1993

[51] Int. Cl.$^6$ ............................................. A61M 16/00
[52] U.S. Cl. .......................... 128/204.23; 128/204.21; 128/205.23; 128/204.18
[58] Field of Search ...................... 128/204.18, 204.21, 128/204.23, 205.23

[56] References Cited

U.S. PATENT DOCUMENTS

| | | | |
|---|---|---|---|
| 4,297,999 | 11/1981 | Kitrell | 128/205.23 |
| 4,957,107 | 9/1990 | Sipin | 128/204.18 |
| 5,044,362 | 9/1991 | Younes | 128/204.23 |
| 5,148,802 | 9/1992 | Sanders et al. | 128/204.23 |
| 5,211,170 | 5/1993 | Press | 128/204.18 |

Primary Examiner—Edgar S. Burr
Assistant Examiner—Aaron J. Lewis
Attorney, Agent, or Firm—Howard J. Greenwald

[57] ABSTRACT

A portable emergency respirator which contains an electrical power supply, a source of compressed air, and a switch which allows one to produce three separate different types of pneumatic outputs from the source of compressed air. In one mode of operation, the output from the source of compressed air provides intermittent positive pressure ventilation to the patient. In a second mode of operation, the output from the source of compressed air is automatically synchronized with the patient's breathing. In a third mode of operation, the output from the source of compressed air is manually controlled by an operator.

20 Claims, 5 Drawing Sheets

PORTABLE EMERGENCY RESPIRATOR

This is a continuation-in-part of applicants' International patent application PCT/US92/02546 (filed on Mar. 26, 1992) for which priority was claimed based upon applicants' U.S. patent application U.S. Ser. No. 07/678,002, which was filed on Apr. 1, 1991 and issued on May 18, 1993 as U.S. Pat. No. 5,211,170.

FIELD OF THE INVENTION

A portable, positive pressure respiratory apparatus is disclosed.

BACKGROUND OF THE INVENTION

Respirators are well known to those skilled in the art. Thus, by way of illustration, one such respirator is described in U.S. Pat. No. 4,215,681 of Zalkin et al. The respirator of this patent is comprised of a reciprocating linear electric motor-compressor having a gas intake orifice connected to atmosphere, a piston, a spring acting on the piston, and an electromagnet for moving the piston against the action of the spring to supply compressed gas to a mask via a discharge orifice. In this device, a thyristor pulse generator is controlled by a clock to provide pulses to the electromagnet to define insufflation time; and the compressor operates only during the insufflation time.

The respiratory apparatus of the Zalkin et al. patent only is capable of providing intermediate positive pressure ventilation, i.e., a pulsed output provided at a specified frequency. However, it is often desirable for a respiratory apparatus to be able to provide an irregular output which is synchronized with a patient's breathing (which output is often referred to as "synchronized intermittent mandatory ventilation"); the apparatus of the Zalkin patent is not capable of providing such irregular, synchronized output.

In certain situations, it is desirable for an operator to be able to manually control the output of a respiratory device, to provide a "continuous positive airway pressure manual cycle". The apparatus of the Zalkin et al. patent is not capable of such manual control and cannot provide such cycle.

Although Zalkin et al. intended to provide "... a respirator of particularly simple design ... " (see column 1), in fact their device is relatively expensive and cumbersome; it does not appear that the Zalkin et al. device is portable. Because of these requirements, it is not believed that the Zalkin et al. apparatus is of the desired "... particularly simple design ... "

In 1985, in U.S. Pat. No. 4,493,614, another respiratory device was disclosed by Raymond D. Chu et al. Although a pump intended for use in portable ventilators is disclosed in this patent, there is no disclosure of a device which is capable of providing either synchronized intermediate mandatory ventilation or the continuous positive airway pressure manual cycle described above.

It is an object of this invention to provide a portable ventilating device which can, in emergency situations, be used in place of mouth-to-mouth resuscitation ("CPR") and thus minimize the risk of spreading infectious disease.

It is yet another object of this invention to provide a portable ventilating device which does not require a separate source of compressed gas, such as oxygen or air.

It is an object of this invention to provide a portable ventilating device which is relatively inexpensive and light-weight.

It is another object of this invention to provide a portable ventilating device which is contains electromechanical means capable of furnishing intermittent positive pressure ventilation, and synchronized intermittent mandatory ventilation, and continuous positive airway pressure.

It is yet another object of this invention to provide a portable ventilating device which is relatively durable and has relatively few moving parts.

SUMMARY OF THE INVENTION

In accordance with this invention, there is provided a respiratory apparatus comprised of a power supply, a respiratory mask, a source of compressed gas, a sensor for sensing the breathing of a patient, and a switch connected to a first pulse generator, a second pulse generator, and a device which will provide manual mode of operation.

BRIEF DESCRIPTION OF THE DRAWINGS

The present invention will be more fully understood by reference to the following detailed description thereof, when read in conjunction with the attached drawings, wherein like reference numerals refer to like elements, and wherein:

FIG. 4 is a graph of the output of the embodiment of FIG. 1, illustrating the various modes which is it capable of operating in;

DESCRIPTION OF THE PREFERRED EMBODIMENTS

Figure 1:
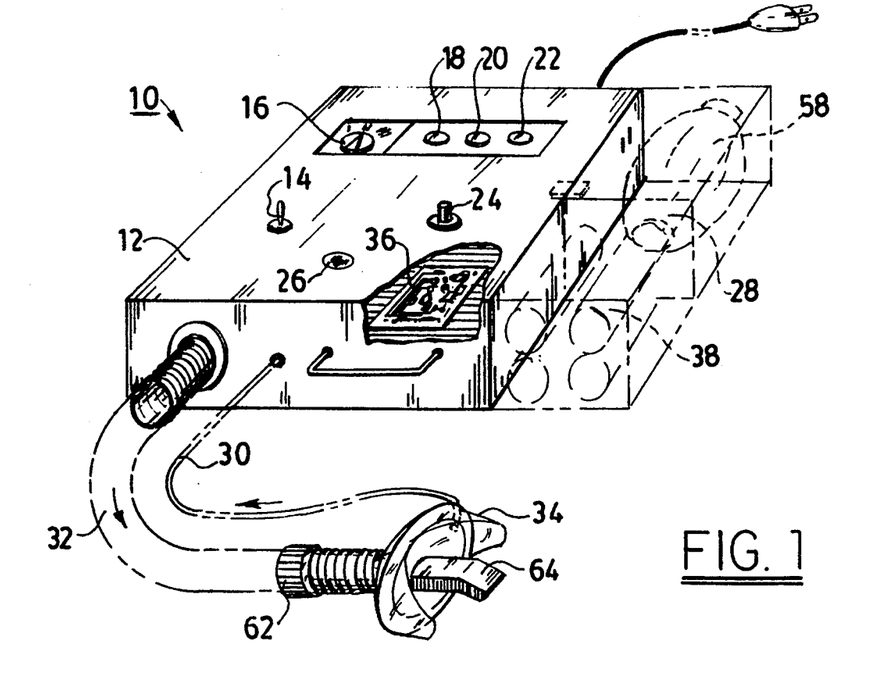
FIG. 1 is a perspective view of one preferred embodiment of the ventilating apparatus of this invention.

Referring to FIG. 1, a preferred embodiment of the portable emergency ventilator 10 of this invention is illustrated. This ventilator 10 is comprised of a case 12, an on-off switch 14, a mode selection switch 16, means 18, 20, and 22 for adjusting the parameters of the breathing pulses produced by ventilator 10, push button switch 24, visual indicator 26, direct current power supply 28, vacuum line 30, tube 32, mask 34, a printed circuit board 36, and a separate, manually-operated resuscitator 58.

Figure 2:
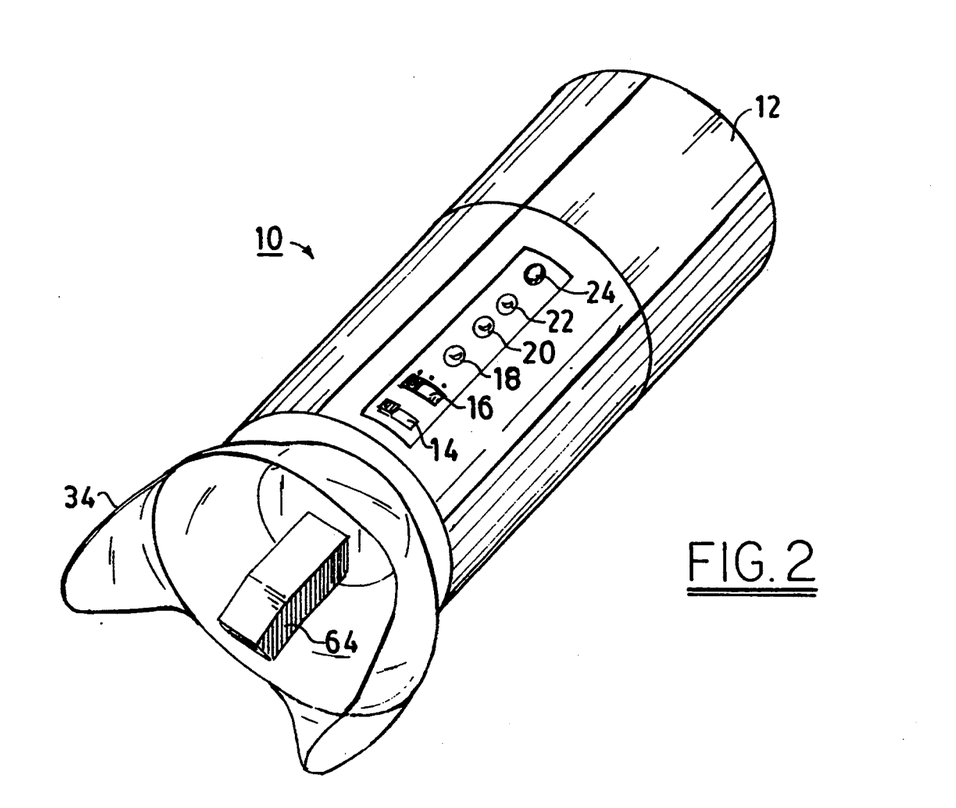
FIG. 2 is a perspective view of another preferred embodiment of the ventilating apparatus of this invention.

Another preferred embodiment of applicant's portable emergency ventilator 10 is illustrated in FIG. 2. Although the apparatus of FIG. 2 has a substantially different shape than that of FIG. 1, it is comprised of substantially the same components.

Figure 3:
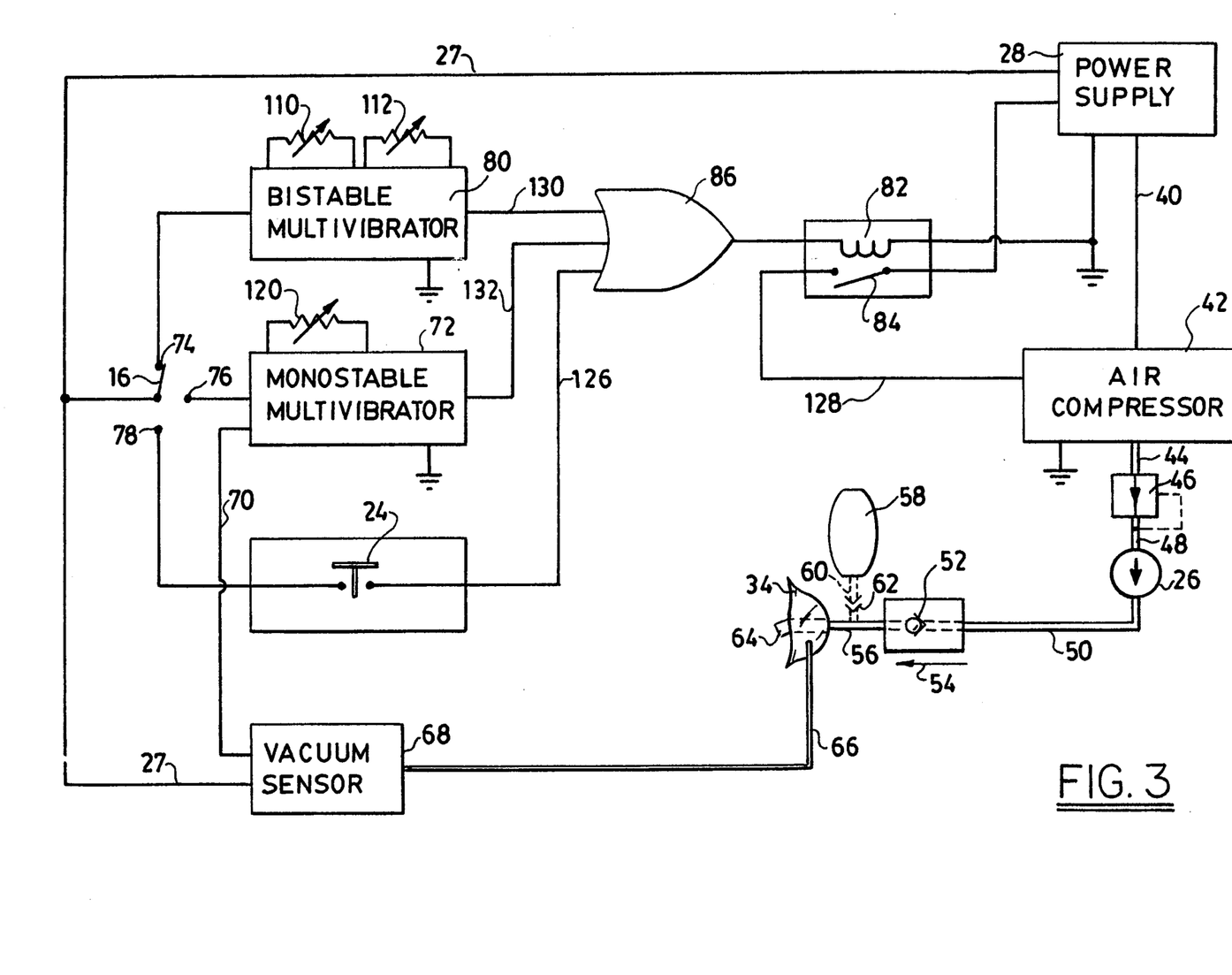
FIG. 3 is a flow diagram of the components comprising the embodiment of FIG. 1.

FIG. 3 is a flow diagram illustrating the components preferably used in the embodiment of FIGS. 1 and 2.

Referring to FIG. 3, it will be seen the ventilating apparatus 10 is comprised of electrical power supply 28.

The power supply 28 may provide direct current and/or alternating current to the device. Thus, in one embodiment, the power supply provides direct current to the control circuit and alternating current to the compressor. Thus, in another embodiment, the power supply provides direct current to both the control circuit and the compressor.

Referring to the preferred embodiment illustrated in FIG. 3, it will be seen that power supply 28, in addition to furnishing power via connecting means 40 to air compressor 42, also provides power via line 27 to the control circuitry. The switch 16, discussed in detail below, determines by its position to which portion of the circuit the power will flow.

In one preferred embodiment, the power supply provides a different power output to the compressor than to the control circuit. In general, the power delivered to the compressor will be from about 10 to 100 times as great as the power delivered to the control circuit. Thus, in this embodiment, the power supply must provide means for delivering at least two different outputs.

The power supply 28 will preferably comprise a means of furnishing direct current to the apparatus; the control circuit, which contains integrated circuitry, requires such direct current. It is preferred that power supply 28 provide from about 5 to about 30 volts of direct current to the device 10. It is more preferred that power supply 28 provide about 12 volts to the control circuit and air compressor in device 10.

The direct current provided to the control circuit will generally flow at a rate of from about 10 to 100 milliamperes and, preferably, from about 20 to about 60 milliamperes. When direct current is provided to the compressor, however, it should flow at a rate of from about 2 to about 8 amperes.

Any means for providing the required direct current may be used in power supply 28. Thus, referring again to FIG. 1, power supply 28 may consist of 8 1.5-volt batteries 38 connected in series. Thus, one might connect the ventilator 10 to an automobile's battery by a connection made through the automobile's lighter socket. Alternatively, or additionally, power supply 28 may comprise transformer and rectifier means (not shown) for converting household alternating current to the required direct current output; these circuits are well known to those skilled in the art and are described, e.g., in Rudolf F. Graf's "The Encyclopedia of Electronic Circuits," Tab Books Inc., Blue Ridge Summit, Penna., 1985 (see, e.g., the circuit of the dual polarity power supply described on page 497).

In one preferred embodiment, the power supply used in ventilator 10 is a line powered supply described on page 48 of Forest H. Mims III's "Engineer's Mini-Notebook: Formulas, Tables, and Basic Circuits" (Radio Shack, Fort Worth, Tex., 1988, catalog number 276–5016).

Power supply 28 is electrically connected, via line 40, to air compressor 42. As indicated above, compressor 42 may be either a direct current compressor or alternating current compressor. Any of the compressors well known to those skilled in the art may be used as compressor 42.

By way of illustration, one may use a compressor of the type having a linear electric motor; see, e.g., U.S. Pat. No. 4,21,5,681, the disclosure of which is hereby incorporated by reference into this specification.

In one preferred embodiment, not shown, the motor and the air compressor unit 42 form a single structure in which only the piston moves inside the cylinder. This structure drives the piston, which reciprocates at a rate in synchronization with the frequency of the alternating current.

In another embodiment, compressor 42 is a rotary vane air compressor. In yet another embodiment, compressor 42 is a multistage air rotary air blower (such as, e.g., that used in a hair dryer). A suitable rotary vane air compressor may be purchased, e.g., from GAST catalog F-10 (May, 1990), which is published by the Gast Manufacturing Corporation of Benton Harbor, Mich. At page 12 of this catalog, the model 1533-102A rotary vane air compressor is one which especially suitable for use in applicant's ventilator.

By way of further illustration, the compressor 42 may be an alternating current compressor which has a linear motor driven free piston mechanism. Such compressors are well known to those in the art and are available, e.g., from Medo U.S.A. Inc., 808-C North Central Avenue, Wood Dale, Ill. 60191. Medo catalog L-001, at page 21, describes a suitable model AC 0601.

The output from compressor 42 is fed via line 44 to pressure valve 46. Pressure valve 46 provides a means for varying the pressure output from air compressor 42.

As is known to those skilled in the art, air compressor 42 is but one means providing a source of compressed gas (such as air, oxygen, or mixtures thereof) to pressure valve 46; and other conventional means may also be used. Thus, by way of illustration and not limitation, one may use bottled gas.

Any of the pressure valves known to those skilled in the art may be used as pressure valve 46.

The output from pressure valve 46 is fed via line 48 to visual indicator 26, which provides a means of illustrating the output delivered to the patient. Any of the visual indicators known to those skilled in the art may be used as indicator 26. Thus, visual indicator 26 may be a gauge. Alternatively, indicator 26 may comprise a spring-loaded ball which is displaced by the flow of air and whose displacement is illustrated through a transparent window.

The output from manual indicator 26 is passed via line 50 to air valve 52. Air valve 52 provides a means for allowing air to flow only in the direction of arrow 54. Any of the non-return valves known to the art may be used as air valve 52. Thus, by way of illustration and not limitation, one may use the Brook Airway Tube model number 591-7305, available from Henry Schein Inc. of 5 Harbor Park Drive, Port Washington, N.Y. 11050.

The output from non-return valve 52 is passed through line 56 to mask 34.

In the preferred embodiment illustrated in FIG. 3, device 10 is provided with a back-up, manually-operated resuscitator 58 which is connected via line 60 to line 56 by means of connector 62. This back-up pump may be used in case of emergency when, for any reason, compressor 42 might cease to provide air to the system. Thus, e.g., if the electrical power should cease being supplied to the system, back-up pump 58 may be used.

Any manual pump may be used as resuscitator 58. Thus, one may use a hand-operated pump, a foot operated pump, and the like.

In one preferred embodiment, resuscitator 58 is comprised of an "Ambu-Resuscitator" (model number 985-3025 or 985-9642), which is a portable, hand-operated resuscitator available from Henry Schein Inc.

The output from non-return valve 54 and/or resuscitator 58 is delivered to mask 34. Any of the masks known to those skilled in the art may be used as mask 34. Thus, e.g., one may use the mask disclosed in U.S.

Pat. No. 4,215,681. Thus, for example, one may use the mask which is part of the Brook Airway Tube (which contains both a non-return valve and a mask and which is described by the aforementioned part number 591-7305 available from Henry Schein Inc.

Mask 34 preferably comprises an air intake line 64 which, preferably, is removably attached to line 56. This air intake line is preferably comprised of an inner air delivery tube and an outer, removable tongue depressor (see FIG. 2). As a patient (not shown) inhales air through line mask 34, a vacuum tends to be created in air intake line 64.

Referring again to FIG. 3, a vacuum line 66 is connected to and communicates with air intake line 64. This vacuum line 66 is operatively connected to a vacuum sensor 68 so that the rhythm and the patient's breathing may be sensed.

Any means for sensing the presence and extent of a vacuum may be used as vacuum sensor 68. By way of illustration, one may use a miniaturized vacuum sensor comprised of a diaphragm and two movable contacts. Such sensors are readily available from, e.g., Micro Pneumatic Logic, inc., 2890 N.W. 62nd Street, Fort Lauderdale, Fla. 33309; see, e.g., the MPL catalog 87500, "Series 500 Pressure Sensors," model number MPL 500-502V.

In one embodiment, applicant's ventilating device preferably contains at least three separate means for providing a pulsed electrical signal which, after being sent to the air compressor (or other source of compressed gas), causes a corresponding pneumatic output. One of these means is preferably comprised of a vacuum sensor. Another of these means is preferably comprised of a switch, such as a manual switch. Switching means are provided for alternatively supplying power to either the first means for generating the pulsed electrical signal, or the second means for generating the pulsed electrical signal, or the third means for generating the pulsed electrical signal. At least two of the means for generating a pulsed electrical signal contain control means for modifying the pulses supplied by them.

The electrical output from vacuum sensor 68 is connected via electrical line 70 to monostable multivibrator 72. In the embodiment illustrated in FIG. 3, where switch 16 is in contact with contact 74, no power flows to multivibrator 72. However, when the switch 16 is moved in contact with contact 76, power does flow to monostable multivibrator 72.

As will be apparent to those skilled in the art, other means for sensing a patient's breathing may be used instead of vacuum sensor 68. Thus, e.g., one may use an air flow sensor such as, e.g., the Microbridge Mass Air Flow Senosr (AWM5000 Series) which is manufactured by the Micro Switch Division of Honeywell Corporation of 11 West Spring Street, Freeport, Ill.

Thus, it will be seen that switch 16 allows one to determine what output will be produced through line air 56. When switch 16 is in contact with contact 74, the bistable multivibrator 80 is caused to operate and to produce a logical signal which, through or-gate 86, will activate electromechanical relay 82, thereby closing relay contact 84 and thus energizing air compressor 42 and/or the valve of on a bottle of compressed gas. When switch 16 is in contact with contact 78, power is allowed to flow to push-button switch 24 which, when activated, allows power to flow through or-gate logical device 86, thereby closing relay contact 84 and thus energizing air compressor 42.

Any of the bistable vibrators and the monostable vibrators known to those skilled in the art may be used in applicant's ventilator 10. Thus, by way of illustration and not limitation, one may use the vibrators described in Forest H. Mims III's "Engineers Mini-Notebook: 555 Timer IC Circuits" (Radio Shack, Fort Worth, Tex., catalog number 276-5010, 1984). The basic monostable vibrator circuit is described on page 6 of this publication, and the basic bistable (also referred to as "astable") circuit is described on page 7 of this publication.

It will be apparent to those skilled in the art that the pulses produced by monostable and/or bistable vibrator circuits also may be produced by other circuits such as, e.g., microprocessors. As long as the output of the circuit is similar to that described in FIG. 4, it may be used in the claimed apparatus.

Figure 4:
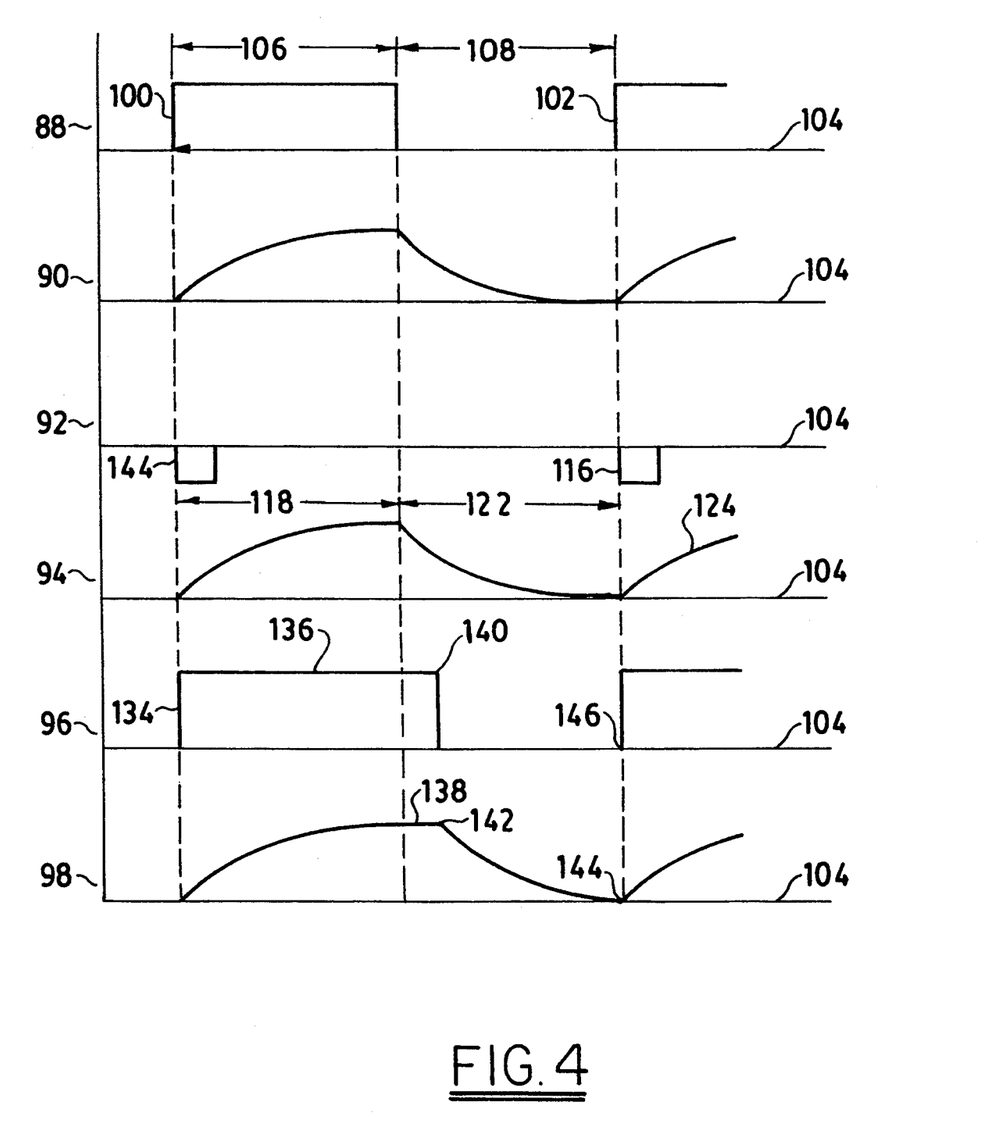

FIG. 4 illustrates the electrical and pneumatic signals obtainable from applicant's device. Electrical signal 88 will tend to produce pneumatic signal 90. Electrical signal 92 will tend to produce pneumatic signal 94. Electrical signal 96 will tend to produce pneumatic signal 98.

Referring again to FIG. 4, it will be seen that electrical signal 88 travels into or-gate 86 when switch 16 is in contact with contact 74. As will be seen by reference to FIG. 4, this electrical signal is comprised of a series of intermittent, periodic pulses 100, 102, etc. The x-axis, 104, is a plot of time.

Each of pulses 100, 102, etc. has a specified duration of inspiratory time, such as, e.g., inspiratory time 106. The interval between adjacent pulses is the expiratory time 108.

In general, the inspiratory time 106 for signal 88 is from about 0.4 to about 4.0 seconds. The expiratory time 108 for signal 88 also can vary from about 0.4 to about 5.0 seconds. The ratio of inspiratory time 108 to expiratory time 106 is generally from about 0.5 to about 2.5.

The time it takes to go through one inspiratory and expiratory cycle (time 106 plus time 108) is referred to as one breathing cycle. In general, applicant's ventilator provides from about 8 to about 66 breathing cycles per minute.

The signal 88 ultimately travels to air compressor 42, whose pneumatic output 90 substantially corresponds to such electrical signal.

The pneumatic signal 90 may be adjusted by varying the characteristics of the electrical signal 88. Thus, e.g., the signal 88 may be varied by adjusting variable resistors 110 and 112. Adjustment of variable resistor 110 will affect the duration of inspiratory time 106. Adjustment of variable resistor 112 will affect the duration of expiratory time 108. Furthermore, inasmuch as frequency is inversely proportional to the sum of times 106 and 108, the adjustment of resistors 110 and 112 will affect the breathing frequency of the user of the device.

It will be understood by those skilled in the art that other means of adjusting the frequency or timing of the electrical output also may be used.

Referring again to FIGS. 3 and 4, it will be seen that electrical signal 92 will be fed to air compressor 42 when switch 16 is in contact with contact 76. In this position, vacuum sensor 68 will generate a series of signals 92 which substantially correspond to the frequency of the patient's breathing.

Referring again to FIG. 4, it will be seen that the signal 92 is comprised of a series of intermittent, periodic square pulses. These signals correspond to the patient's inhalation. Each inhalation will create one monostable pulse such as, e.g., pulse 114.

The inspiratory time 118 of the pneumatic signal 94 may be varied by adjusting variable resistor 120 of monostable vibrator 72 (see FIG. 3). The expiratory time 122 will depend upon when the patient next inhales and thus generates pulse 116; as soon as this occurs, the next inspiratory cycle 124 will occur.

When switch 76 is in contact with contact 78, the output from air compressor 42 may be manually controlled by the operator. This may be done by depressing normally open push-button switch 24.

Any conventional normally open switch may be used as switch 24. When normally open switch 24 is closed such as, e.g., by depressing it, an electrical signal will be sent through connecting means 126 to or-gate 86 and then will activate relay 84, causing power to be furnished to air compressor 42 through connecting means 128. It will be apparent that the electrical signals from the bistable multivibrator 80 and the monostable multivibrator 72 are transmitted through similar means via lines 130 and 132, respectively, to or-gate 86 and then, in a similar manner, to air compressor 42.

It will be understood that other means of insuring one-way transmission of electrical signals may be used instead of or-gate 86. Thus, for example, one may use one or more diodes (not shown), and/or other logical devices.

Referring again to FIG. 4, it will be seen that signal 96 at point 134 when switch 24 is moved to the closed position. Thereafter, as long as said switch 24 is closed, pulse 136 is generated, and a corresponding inspiratory pneumatic pulse is provided to the patient. Once the switch 24 is moved to the open position (see point 140), however, the pulse 136 ceases being generated, and the expiratory portion of the breathing cycle commences(-see point 142). One can then start the inspiratory cycle again (at point 144) by depressing the switch 24 again (at point 146).

In one embodiment, not shown, the electrical circuitry discussed above is electrically and mechanically connected to a bottle of compressed gas and regulates the flow of gast therefrom.

The respirator 10 of this invention is relatively lightweight, preferably weighing less than about 20 pounds. In a more preferred embodiment, it weighs less than about 16 pounds.

Because of its portability and ease of use, the respirator 10 may be used in many situations in which mouth to mouth resuscitation currently is being used. As is known to those skilled in the health care art, mouth-to-mouth resuscitation may result in the spread of infectious diseases, said as the Acquired Immune Deficiency Disease. The size of applicant's device, and its flexibility, allows its ready uses by policemen, lifeguards, nurses, and other personnel in a variety of settings and circumstances wherein the prior art respirators could not be readily used. Thus, by way of illustration, applicants' respirator can readily be used on a battlefield, in an ambulance, on a beach, on an airplane, and the like. Furthermore, patients who suffer from breathing insufficiency diseases (such as asthma) can carry applicants' device with them and use it whenever the occasion demands.

Figure 5:
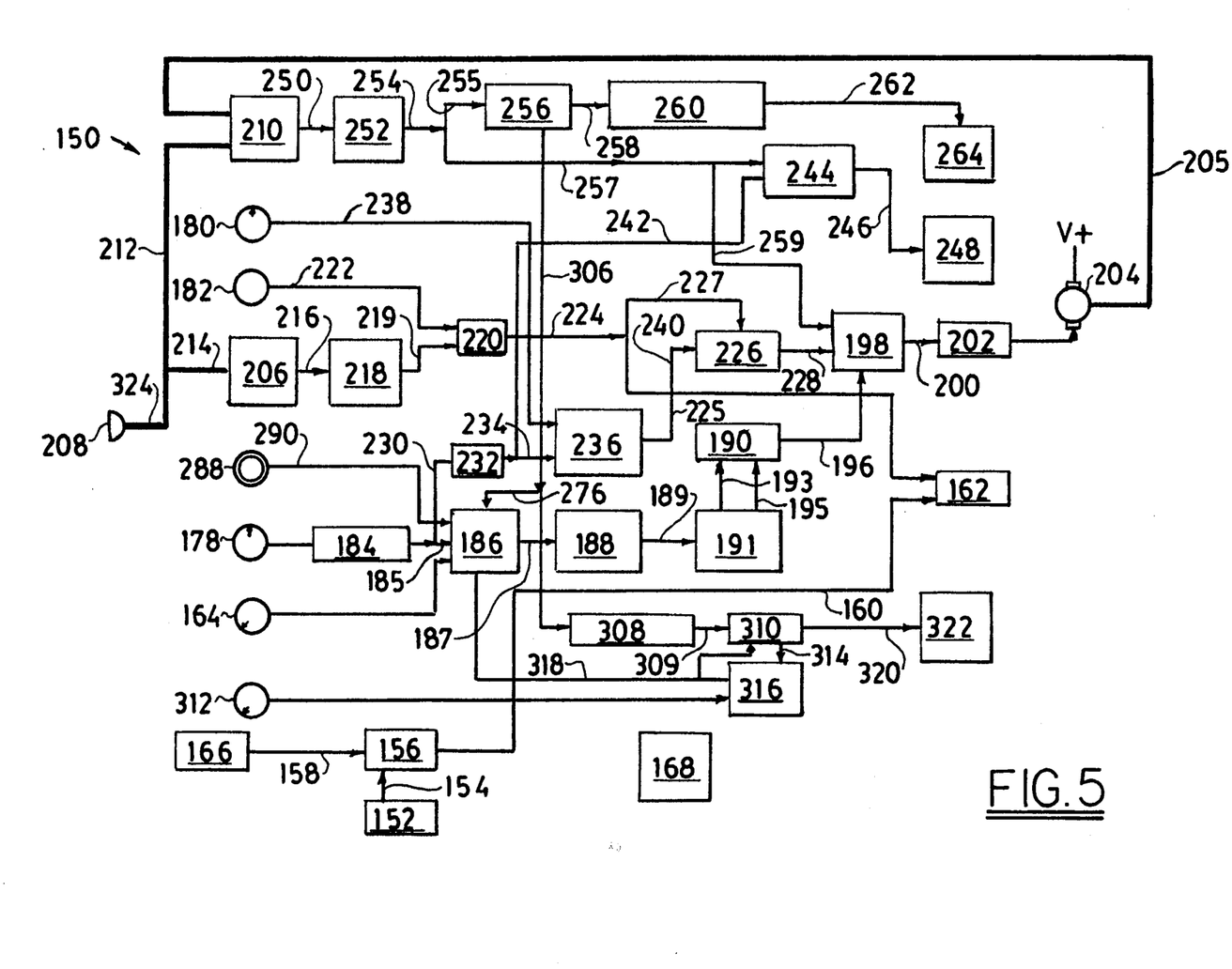
FIG. 5 is a block diagram depicting another preferred embodiment of applicants' ventilating apparatus.

FIG. 5 is a block diagram illustrating another preferred embodiment of applicants' ventilating apparatus whose operation may be automatically varied depending upon the volume of air flowing to or from the user of the device. By comparison, the operation of the apparatus of FIG. 1 varied depending upon the pressure of air flowing to or from the device's user.

Referring to FIG. 5, it will be seen that the ventilator 150 is preferably powered by a self-contained battery 152, which furnishes power via line 154 to voltage controller 156. The power may be turned on by a power switch (not shown), and the power preferably flows through a ten ampere circuit breaker (not shown). Referring to FIG. 5, the power flows through line 158 to controller 156.

The output from voltage controller 156 is fed via line 160 to an audio/visual alarm 162; thus, alarm 162 will beep and/or display a visual warning when the battery 152 needs charging.

Mode switch 164 controls the mode which the ventilator 150 is in. When mode switch 164 is in the off position, and the power switch (not shown) is in the on position, the external power source 166 is used to charge the battery 152. It is preferred that, due to current levels, the external power source 166 not be used to charge the battery 152 with the ventilator 150 running. The voltage controller 156 controls the external power, regulates battery charging, and provides circuit power. In the embodiment illustrated in FIG. 5, elapsed time indicator 168 accumulates run time to hundredths of hours.

Figure 6:
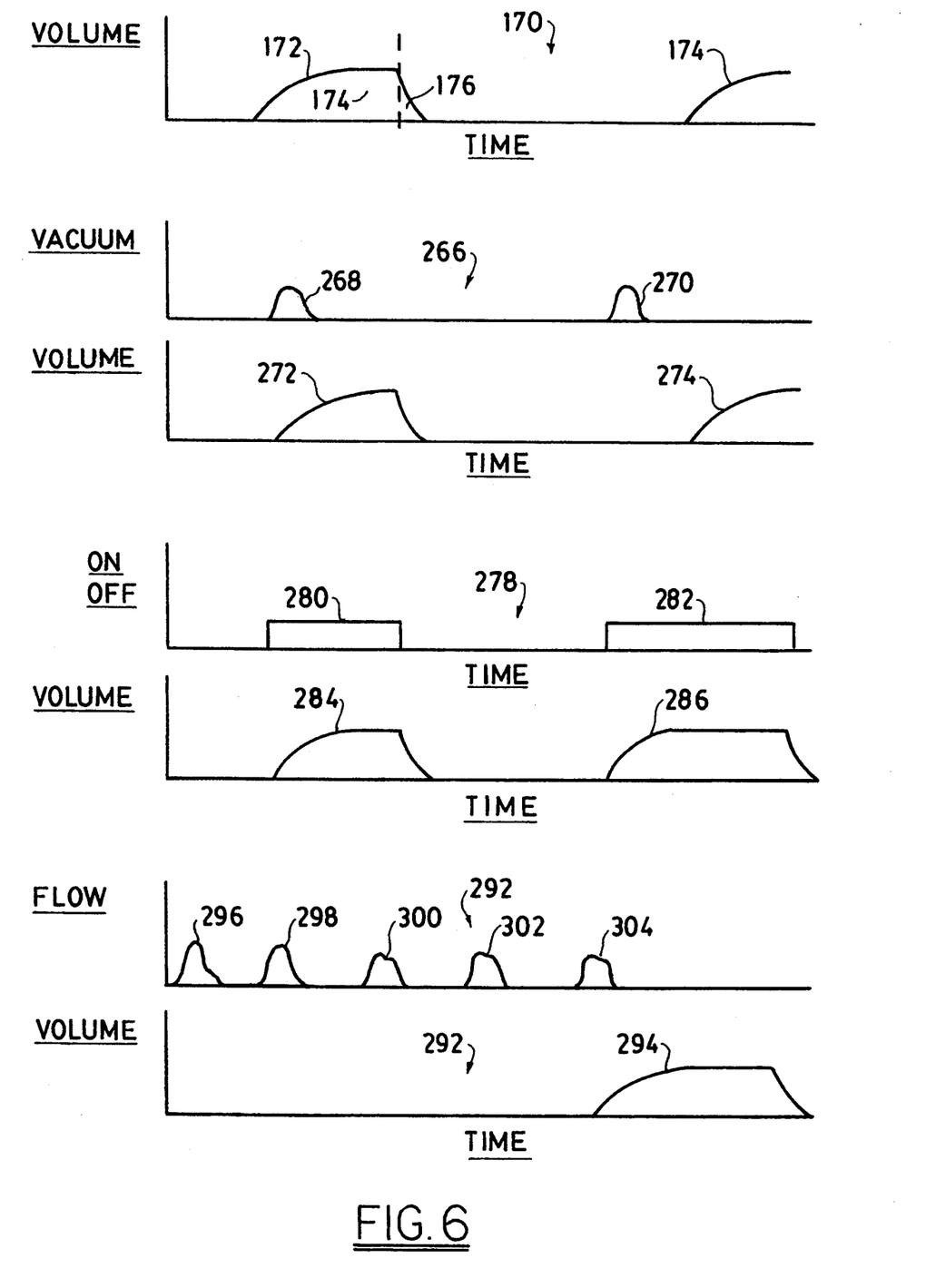
FIG. 6 is a graph of the output of the embodiment of FIG. 5, illustrating the various modes in which it is capable of operating.

The ventilating apparatus 150 provides a substantial amount of flexibility in allowing the operator thereof to choose between numerous modes of operation, which are illustrated in FIG. 6.

Referring to FIG. 6, it will be seen that ventilator 150 can be operated in mode 170, often referred to as the "common mode ventilation," in which the delivered tidal volume (in liters) varies with time (in seconds).

A breathing pulse 172 is illustrated in FIG. 6. The ratio of the inhalation portion 174 of the pulse 172 to the exhalation portion 176 of the pulse 172, can be varied in mode 1. In one preferred embodiment, the ratio of inhalation portion 174 (seconds) to exhalation portion 176 (seconds) is from about is from about 0.3/1.0 to about 0.7 to 1.0 and, more preferably, from about 0.4/1.0 to about 0.6/1.0.

Referring again to FIG. 5, it will be seen that the ventilation obtainable in mode 170 may be determined by setting the breaths/minute switch 178 (which may, e.g., be a potentiometer) and the volume switch 180 (which also may, e.g., be a potentiometer). The volume switch 180 will set the number of liters per breath delivered by the ventilator 150.

The pressure adjustor 182, whose operation is described below, sets the maximum pressure of the air to be delivered to the patient's lungs.

In one preferred embodiment, illustrated in FIG. 5, the breaths/minute adjustor 178 sets the rate of oscillator 184 to a frequency which preferably is equal to about 1,000 times the breath per second rate. As will be apparent to those skilled in the art, other frequencies also may be used.

Referring again to FIG. 5, and in the preferred embodiment illustrated therein, it will be seen that the frequency of oscillator 184 is gated through the digital logic gates 186 via line 185 and then fed to counter 188 via line 187. The counter 188 accumulates the output pulses from oscillator 184 for a specified number of pulses per breath such as, e.g., 1,000 pulses; and information from counter 188 is fed via line 189 to decoder 191. Decoder 191 thereafter feeds information via lines 193 and 195 to flip-flop circuit 190. Information regarding the inspiratory pulse 174 is fed via line 193, and information regarding the expiratory pulse 176 is fed via line 195.

The ratio of inspiratory to expiratory time is preferably about 0.5/1.0 (see FIG. 6). The inspiratory portion 174 of pulse 172 (see FIG. 6) starts at a count of 1 and ends a count of 333, and the expiratory portion of pulse 172 starts at a count of 334 and ends at a count of 999. The cycle then repeats again at 1, with the initiation of the second inspiratory pulse. When the counter 188 reaches 334, flip-flop circuit 190 is furnished information from decoder 191 via line 195. When the counter 188 is reset at 1 after reaching 999, flip-flop circuit 190 is furnished information from decoder 191 via line 193.

During the inspiratory portion 174 of cycle 172, flip flop 190 feeds information via line 196 to pulse width modulator 198. As is known to those skilled in the art, the pulse width modulator controls the amount of power delivered to a device and, thus, the output of the device.

The pulse width modulator 198 is operated only when it is being fed information via line 196. When pulse width modulator 198 is on, it feeds a signal via line 200 to driver 202, thus causing driver 202 to operate air pump 204. Inasmuch as the signal fed to pulse width modulator 198 via line 196 is variable, the output of pulse width modulator 198 varies, and the amount of air delivered by air pump 204 per unit time also varies.

In the embodiment illustrated in FIG. 5, pressure sensor 206 can cause information to be fed to pulse width modulator 198 which, when the pressure is excessive, will cause the pulse width modulator 198 to direct air pump 204 to reduce the air flow.

Air pump 204 feeds air via line 205 to flow meter 210. Flow meter 210 measures the air flow rate (in liters per minute) and causes a display of such information in a manner to be described later. Air from flow meter 210 is delivered via line 212 to mask 208, which can be utilized by the patient (not shown).

A portion of the air flowing through line 212 feeds via line 214 to pressure sensor 206, which feeds information regarding the pressure in line 214 via line 216 to a signal conditioning circuit 218, which transforms the signal into a form suitable for use by comparator 220. The signal from conditioning circuit 218 is fed via line 219 to comparator 220. A signal from pressure adjuster 182 is fed via line 222 to comparator 220. Comparator 220 then compares the pressure setting (from adjuster 182) with the actual pressure in line 214 and, when the latter exceeds the former, sends a signal via lines 224 and 225 to alarm circuit 162 (thereby actuating said alarm) and via lines 224 and to overpressure cutoff circuit 226.

The overpressure cutoff circuit 226 controls the pulse width modulator 198, feeding information to it via line 228.

Ventilator 150 also contains means for controlling the rate of air flow to the patient (in, e.g., liters per minute delivered). In the embodiment illustrated in FIG. 5, this may be done by controlling the breaths per minute adjustment and the liters per breath adjustment. As will be apparent, the product of breaths per minute times liters per breath is liters/per minute.

Referring to FIG. 5, the oscillator 184 feeds a signal via lines 185 and 230 to a frequency/voltage converter 232, which generates an analog signal proportional to the frequency of the oscillator signal. The oscillator signal is proportional to the setting of breaths/minute adjuster 178.

The frequency/voltage converter 232 feeds an analog signal via line 234 to voltage multiplier 236, which multiplies the signal from converter 232 with the signal from liters/breath adjuster 180 (which feeds its signal to voltage multiplier 236 via line 238). When the product of the two signals exceeds a certain specified value, a signal is then fed from voltage multiplier 236 via line 240 to overpressure cutoff circuit 226, which operates in the manner described above.

In the embodiment illustrated in FIG. 5, the output from frequency/voltage converter 232 also is preferably fed via line 242 to voltage divider 244 which divides actual air flow by breaths per minute to obtain liters per breath. A signal from voltage divider 244 is fed via line 246 to display 248. Display 248 displays liters per breath.

As indicated above, air flow sensor 210 determines the air flow and sends a signal via line 250 to signal conditioning circuit 252, which provides an analog signal of the measured air flow suitable for use in subsequent stages.

A signal from conditioning circuit 252 is fed via line 254 to both flow direction analyzer 256 (via line 255) voltage divider 244 (via line 257), and pulse width modulator 198 (via line 259). This information represents the desired air flow rate to the pulse width modulator 198. Desired air flow rate is compared with measured air flow rate (obtained in a manner described later in this specification) in the pulse width modulator 198. If the measured air flow rate is more than the desired air flow rate, the pulse width modulator reduces the signal to the driver 202 thus reducing the air flow. If the measured air flow rate is less than the desired air flow rate, the pulse width modulator 198 increases the signal to the driver 202.

F direction analyzer 256 determines whether the air flow is positive (i.e., towards the patient) or negative (from the patient). When the flow is positive, it feeds a signal via line 258 to digital signal conditioner 260, which scales the signal and feeds the signal so scaled via line 262 to breaths per minute indicator 264, where it may be digitally displayed.

Referring again to FIG. 6, mode 266 allows the patient's gasp to control the operation of ventilator 150. In this mode 266, a patient's gasp to draw air triggers a single respiratory cycle. Each of the patient's gasps 268 and 270 causes a corresponding inhalation/exhalation cycle 272 and 274, which commence immediately after the respective gasp.

Referring again to FIG. 5, the mass flow sensor 210 and the signal conditioning circuit 252 provide a signal to digital logic gates 186 via line 276. The digital logic gates 186 triggers the counter 188 for one respiration cycle per gasp. Each subsequent gasp for air will trigger one corresponding respiration cycle. In the absence of such a patient's gasp, the minimum time to the next ventilation cycle will be set by the breaths per minute control 178.

Referring again to FIG. 6, mode 278 is a manually controlled mode in which on-off pulses 280 and 282 generate corresponding inhalation/exhalation pulses 284 and 286 from ventilator 150.

Referring again to FIG. 5, it will be seen that manual push button 288 is electrically connected via line 290 to digital logic gates 186, which in turn control counter 188 (and, ultimately, the pulse width modulator 198 in the manner described elsewhere in this specification). If, while in mode 278, push button 288 is not pushed for a specified minimum time, the minimum time to the next ventilation cycle will then be controlled by the breaths per minute control 178.

Referring again to FIG. 6, it will be seen that ventilator 150 also may be operated in the cardio-pulmonary-resuscitation ("CPR") mode 292. In this mode 292, when a CPR is being administered to a patient, the machine automatically will furnish a pulse of air after a fixed number of compressions of the patient's chest. Thus, referring to FIG. 6, it will be seen that pulse 294 will be delivered by ventilator 150 after five chest compressions 296, 298, 300, 302, and 304 have been delivered to the patient.

One preferred means of producing mode 292 is illustrated in FIG. 5. Referring to FIG. 5, when a patient's chest is manually compressed by CPR, the patient will be forced to exhale. This exhalation will be sensed by flow direction analyzer 256 which will then furnish a signal via line 306 to differentiator 308. Differentiator 308 will determine whether the rate of change of flow is substantial enough (and, thus, is consistent with the chest compression associated with CPR), and will furnish information regarding the number of CPR pulses to counter 310 via line 309. When the counter 310 reaches a certain predetermined number of pulses set by CPR controller 312 (such as, e.g., the five pulses depicted in FIG. 6), the counter 310 will then send a signal via line 314 decoder 316. The decoder 316 will, in turn, send a signal via line 318 to logic gates 186 which, as described elsewhere, will ultimately cause pulse width modulator 198 to operate air pump 204 and to deliver air to the patient.

In addition, counter 310 will deliver a signal via line 320 to display 322.

In one preferred embodiment, not shown, supplemental oxygen is supplied to the ventilator 150 by conventional means. Thus, referring to FIG. 5, venturi T-adaptors (not shown) may be provided at various points in line 212 such as, for example, point 324. To one or more of these venturi T-adaptors may be connected oxygen containers (such as oxygen bottles, or oxygen tanks) which will feed oxygen into the system as air flows past the venturi. As is known to those skilled in the art, various flow rates of oxygen are afforded by various commercially available oxygen venturis.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims. Thus, by way of illustration, it will be understood that the various electronic means depicted in FIGS. 1 and 5 can be replaced, in whole or in part, by microprocessor circuitry.

We claim:

1. A portable emergency ventilating apparatus, wherein said ventilating apparatus is comprised of:
   (a) an electrical power supply;
   (b) a source of compressed gas;
   (c) a first means for producing a pulsed electrical signal, wherein said first means for producing an electrical signal is comprised of a timing circuit;
   (d) a second means for producing a pulsed electrical signal, wherein said second means for producing a pulsed electrical signal is comprised of means for sensing a patient's breathing;
   (e) a third means for producing a pulsed electrical signal, wherein said third means for producing a pulsed electrical signal is comprised of a first switching means, and wherein said first switching means is comprised of a switch;
   (f) second switching means for alternatively supplying power to said first means for producing a pulsed electrical signal, said second means for producing a pulsed electrical signal, and said third means for producing a pulsed electrical signal, wherein said second switching means is electrically connected to said power supply; and
   (g) means for sending said pulsed electrical signal to said source of compressed gas.

2. The ventilating apparatus as recited in claim 1, wherein said apparatus is comprised of means for sensing compression of a patient's chest.

3. The ventilating apparatus as recited in claim 2, wherein said apparatus is comprised means for counting compressions of a patient's chest.

4. The ventilating apparatus as recited in claim 3, wherein said source of compressed gas is an air compressor, and said apparatus is comprised of means for delivering a pulsed electrical signal to said air compressor after it has counted a specified number of compressions of a patient's chest.

5. The ventilating apparatus as recited in claim 4, wherein said apparatus is comprised of means for varying the number of compressions of a patient's chest which must be sensed by the apparatus prior to the time said pulsed electrical signal is delivered to said air compressor.

6. The apparatus as recited in claim 5, wherein said apparatus is comprised of means for measuring the amount of air flowing from said air compressor to a patient.

7. The apparatus as recited in claim 6, wherein said apparatus is comprised of means for measuring the amount of air flowing from said patient towards said air compressor.

8. The apparatus as recited in claim 7, comprised of means for comparing the amount of air flowing from said air compressor to said patient with a specified tidal volume reference standard.

9. The apparatus as recited in claim 8, wherein said apparatus is comprised of means for varying said tidal volume reference standard.

10. The apparatus as recited in claim 9, comprised of means for increasing the amount of air flowing from said air compressor to said patient whenever said amount of air is less than said tidal volume reference standard.

11. The apparatus as recited in claim 10, comprised of means for measuring the pressure of air flowing from said air compressor to said patient.

12. The apparatus as recited in claim 1, wherein said apparatus is comprised of means for measuring the amount of air flowing from said source of compressed gas to a patient.

13. The apparatus as recited in claim 12, wherein said source of compressed gas is an air compressor, and wherein said apparatus is comprised of means for measuring the amount of air flowing from said patient towards said air compressor.

14. The apparatus as recited in claim 13, comprised of means for comparing the amount of air flowing from said air compressor to said patient with a specified tidal volume reference standard.

15. The apparatus as recited in claim 14, wherein said apparatus is comprised of means for varying said tidal volume reference standard.

16. The apparatus as recited in claim 15, comprised of means for increasing the amount of air flowing from said air compressor to said patient whenever said amount of air is less than said tidal volume reference standard.

17. The apparatus as recited in claim 16, comprised of means for measuring the pressure of air flowing from said air compressor to said patient.

18. The apparatus as recited in claim 17, comprised of means for activating an alarm whenever said air pressure is less than said pressure reference standard.

19. The apparatus as recited in claim 17, comprised of means for comparing the pressure of air flowing from said air compressor to said patient with a specified pressure reference standard.

20. The apparatus as recited in claim 19, comprised of means for ceasing the flow of air from said air compressor whenever the pressure of said flowing air exceeds said specified pressure reference standard.

* * * * *